United States Patent
Taneichi et al.

(10) Patent No.: US 6,844,481 B2
(45) Date of Patent: Jan. 18, 2005

(54) SHEET FOR ABSORBENT ARTICLE AND ABSORBENT ARTICLE USING THE SAME

(75) Inventors: Shoichi Taneichi, Tochigi (JP); Yasuhiro Komori, Tochigi (JP); Manabu Kaneda, Tochigi (JP); Shinsuke Nagahara, Tochigi (JP); Tetsuyuki Kigata, Tochigi (JP); Yayoi Fukuhara, Tochigi (JP); Masahito Tanaka, Tochigi (JP); Minoru Nakanishi, Tochigi (JP)

(73) Assignee: Kao Corporation, Tokyo (JP)

( * ) Notice: Subject to any disclaimer, the term of this patent is extended or adjusted under 35 U.S.C. 154(b) by 74 days.

(21) Appl. No.: 09/794,145

(22) Filed: Feb. 28, 2001

(65) Prior Publication Data

US 2001/0031953 A1 Oct. 18, 2001

(30) Foreign Application Priority Data

Feb. 28, 2000 (JP) ........................... 2000-052587
Mar. 30, 2000 (JP) ........................... 2000-094230

(51) Int. Cl.$^7$ .................................. A61F 13/15
(52) U.S. Cl. .................. 604/366; 604/370; 604/365
(58) Field of Search ................. 604/366, 370, 604/365, 385.16, 385.22, 367, 379, 383; 442/199–202, 212–216, 334, 361–365; 428/375, 374, 373

(56) References Cited

U.S. PATENT DOCUMENTS

| | | | |
|---|---|---|---|
| 3,760,046 A | * 9/1973 | Schwartz et al. | 264/46.1 |
| 4,623,340 A | * 11/1986 | Luceri | 604/385.05 |
| 4,648,876 A | * 3/1987 | Becker et al. | 604/370 |
| 4,794,038 A | * 12/1988 | Marcus | 428/288 |
| 4,842,595 A | 6/1989 | Nakanishi et al. | |
| 5,167,765 A | * 12/1992 | Nielsen et al. | 162/146 |
| 5,169,580 A | * 12/1992 | Marcus | 264/115 |
| 5,272,023 A | * 12/1993 | Yamamoto et al. | 428/198 |
| 5,324,561 A | 6/1994 | Rezai et al. | |
| 5,336,552 A | * 8/1994 | Strack et al. | 442/361 |
| 5,405,682 A | * 4/1995 | Shawyer et al. | 428/221 |
| 5,591,150 A | 1/1997 | Olsen et al. | |
| 5,674,341 A | 10/1997 | Ng | |
| 5,800,230 A | 9/1998 | Horiuchi et al. | |
| 5,804,286 A | * 9/1998 | Quantrille et al. | 428/198 |
| 5,876,840 A | * 3/1999 | Ning et al. | 428/198 |
| 5,913,850 A | * 6/1999 | D'Alessio et al. | 607/378 |
| 5,989,688 A | * 11/1999 | Barge et al. | 428/198 |
| 6,156,024 A | 12/2000 | Schulte et al. | |
| 6,156,679 A | * 12/2000 | Takaoka et al. | 442/327 |

FOREIGN PATENT DOCUMENTS

| | | |
|---|---|---|
| CN | 1178267 A | 4/1998 |
| CN | 1189999 A | 8/1998 |
| EP | 0 858 791 A2 | 8/1998 |
| JP | 63-117753 A | 5/1988 |
| JP | 08 24289 | 1/1996 |
| JP | 10-216172 A | 8/1998 |
| JP | 11192259 | 7/1999 |
| TW | 270903 | 2/1996 |
| TW | 266281 | 8/1999 |
| TW | 366287 | 8/1999 |

\* cited by examiner

*Primary Examiner*—Jacqueline Stephens
(74) *Attorney, Agent, or Firm*—Birch, Stewart, Kolasch & Birch, LLP (57) ABSTRACT

A sheet which gives an absorbent article improved recovery from distortion is disclosed. The sheet has a recovery force of 0.7 cN or more in the cross direction, a compressive strength of 100 cN or less, and a basis weight of 20 g/m$^2$ or more.

15 Claims, 2 Drawing Sheets

SHEET FOR ABSORBENT ARTICLE AND ABSORBENT ARTICLE USING THE SAME

BACKGROUND OF THE INVENTION

1. Field of the Invention

The present invention relates to a sheet for absorbent articles. More particularly, it relates to a sheet which can provide absorbent articles, such as sanitary napkins, panty liners, and adult incontinence pads, which are prevented from distortion while worn, have an improved fit to a wearer's body, and hardly cause leakage. The present invention also relates to an absorbent article using the same.

2. Description of the Related Art

Various types of sheets for use in absorbent articles have been proposed aiming at preventing absorbent articles from distortion. For example, Japanese Patent Laid-Open No. 24289/96 proposes using nonwoven fabric comprising hollow synthetic fibers having a specific average diameter as a material making an absorbent member to provide an absorbent article resistant to distortion. While the proposed nonwoven fabric is capable of producing a cushioning effect in the thickness direction, it fails to improve resistance to distortion in the planar direction, still involving reduction in fit to a wearer's body and in leakproofness due to the distortion.

Various improvements have been added to absorbent articles for improving resistance to distortion and preventing leakage, such as use of nonwoven fabric comprising fibers having elasticity recovery properties (24289/96 supra) and disposition of a second sheet having a high rate of absorption between a topsheet and an absorbent member (Japanese Patent Laid-Open No. 192259/99). However, none of the absorbent articles heretofore proposed is not sufficient for prevention of distortion while it is worn, which has led to loss of fit to a wearer's body and leakproofness.

SUMMARY OF THE INVENTION

An object of the present invention is to provide a sheet for an absorbent article which, when used in an absorbent article, is capable of effectively preventing the absorbent article from being distorted or twisted in the planar direction as worn thereby securing comfort, a good fit to a wearer's body, and leakproofness; a process of producing the sheet; and an absorbent article using the same.

The inventors of the present invention have found that a sheet exhibiting excellent recovery in a specific direction, when used in an absorbent article, is effective to prevent distortion of the article.

The present invention, completed based on the above finding, includes first to third aspects. The first aspect of the present invention relates to a sheet that can provide an absorbent article with improved recovery from distortion, which sheet has a recovery force of 0.7 cN or more in the cross direction (CD), a compressive strength of 100 cN or less, and a basis weight of 20 g/m² or more.

The second aspect of the present invention relates to a process of producing a sheet for an absorbent article, which sheet comprises thermally bonded nonwoven fabric comprising 70% by weight or more of specific core-sheath type thermally bonding conjugate fibers, which are thermally fused together at their intersections, wherein the process includes a step of heat treating a fiber web and a step of compressing (a) the fiber web before being heat-treated or (b) a thermally bonded nonwoven fabric obtained by heating the fiber web to reduce the thickness of the fiber web (a) or the thermally bonded nonwoven fabric (b) to 20 to 80% of the original thickness.

The third aspect of the present invention relates to an absorbent article comprising a liquid retentive absorbent layer and a liquid impermeable leakproof layer, wherein the absorbent layer has the above-described sheet.

Another object of the invention is to provide an absorbent article which is not distorted while worn thereby securing a good fit to a wearer's body, and leakproofness.

The above object is accomplished by a fourth aspect of the invention. The fourth aspect of the invention relates to an absorbent article which has substantially longitudinal shape and comprises a liquid retentive absorbent layer and a liquid impermeable leakproof layer, wherein the absorbent layer has a surface layer that is to be brought into contact with a wearer's skin and an elastic layer disposed under the surface layer, the elastic layer having an elastic recovery force of 0.7 cN or more, and the absorbent article has a compressive strain of less than 5% in the width direction thereof.

The sheet according to the first aspect of the invention provides an absorbent article which is resistant to distortion in the planar direction, feels comfortable to wear, and has improved leakproofness.

The process of producing the sheet of the first aspect, which constitutes the second aspect of the present invention, makes it possible to prepare an absorbent article which has the above described excellency easily and simply without causing buckling in roll or stiffness reduction.

The absorbent article according to the third and fourth aspects of the invention is not liable to distortion while worn, securing a good fit to a wearer's body and leakproofness.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be more particularly described with reference to the accompanying drawings, in which.

DETAILED DESCRIPTION OF THE PREFERRED EMBODIMENTS

The first to third aspects of the present invention will be described. The sheet for absorbent articles according to the present invention serves to improve recovery of an absorbent article from distortion.

The term "recovery from distortion" as used herein means a property of an absorbent article for restoring the initial shape even when it is warped, turned up or twisted by external force while being worn.

The sheet for absorbent articles has a recovery force of 0.7 cN or more, preferably 2.0 to 6.0 cN in the cross direction (CD), a compressive strength of 100 cN or less, preferably 10 to 100 cN, and a basis weight of 20 g/m² or more, preferably 20 to 50 g/m², still preferably 30 to 45 g/m².

If the recovery force in the CD is less than 0.7 cN, the effect on recovery from distortion is not sufficient. If the compressive strength is more than 100 cN, the comfort and the fit on wearing reduce.

If the basis weight is less than 20 g/m², the effect on recovery from distortion is not manifested. From the standpoint of productivity and cost, the basis weight is preferably less than 50 g/m².

The sheet for absorbent articles preferably has a thickness of 1.0 mm or smaller, particularly 0.3 to 0.8 mm, for securing the comfort on wearing and the fit to a wearer's body.

The recovery force in CD, thickness, and compressive strength of the sheet according to the present invention are measured as follows. The term "cross direction (CD)" as used herein means a direction substantially perpendicular to the fiber orientation direction (machine direction; MD). That is, the sheet of the present invention exhibits a recovery property from deformation in the CD.

Measurement of Recovery Force in CD:

A 45 mm wide and 145 mm long strip is cut out of a sheet with the width direction of the strip agreeing with the CD of the sheet. The strip is rolled with its length in the peripheral direction to make a cylinder of 40 mm in diameter. The lap is fastened with staples at three positions 10 mm apart from each other.

The cylindrical test specimen is set on a compression tester RTM-100, manufactured by Toyo Baldwin, (initial specimen height: 45 mm) and compressed under a compression plate at a compressing speed of 50 mm/min in the axial direction of the cylinder (downstroke). After compressing the specimen by a 15 mm downstroke, the compressing plate was then moved upward to the initial sample height of 45 mm (upstroke). The load vs. the stroke distance in the up-and-down double stroke was recorded, and the load at 2 mm before the distance of zero load in the upstroke is read, which is taken as a recovery force in the CD.

Measurement of Thickness:

The thickness of the sheet was measured with a thickness meter (a constant load thickness meter PG-11, manufactured by Techloc) under a constant load of 0.36 kPa.

Measurement of Compressive Strength:

A cylindrical test specimen prepared in the same manner as described above is set in a compression tester (initial sample height: 45 mm). The specimen was compressed with a compressing plate at a speed of 50 mm/min, and the maximum load applied was measured.

The sheet satisfying all the above requirements preferably includes, but it not limited to, nonwoven fabric A and nonwoven fabric B described below.

Nonwoven Fabric A:

Thermally bonded nonwoven fabric comprising 70% by weight or more of core-sheath type thermally bonding conjugate fibers which are thermally fused together at their intersections, wherein the core comprises an olefin polymer, polyester, or polyamide, and the sheath comprises (1) a copolymer mainly comprising propylene, (2) a copolymer mainly comprising ethylene, or (3) low-density polyethylene.

Nonwoven Fabric B:

Thermally bonded nonwoven fabric comprising 70% by weight or more of core-sheath type thermally bonding conjugate fibers which are thermally fused together at their intersections, wherein the core comprises polyester or polyamide, the sheath comprises high-density polyethylene, and the conjugate fibers have an average fineness of 6.6 dtex to 22 dtex.

Nonwoven fabrics A and B will be described below. First, nonwoven fabric A will be described. The olefin polymer which can be used as a core of the core-sheath type thermally bonding fibers making up nonwoven fabric A includes a propylene homopolymer and a copolymer mainly comprising propylene and, as a minor component, ethylene or other α-olefins and having a degree of crystallinity of 40% or more.

The polyester which can be used as a core of the thermally bonding fibers making nonwoven fabric A includes polyethylene terephthalate, polybutylene terephthalate, polyethylene naphthalate, polyhexamethylene terephthalate, polytetramethylene terephthalate, poly-1,4-dimethylcyclohexane terephthalate, and polypivalolactone t, and copolyesters comprising any one or more of the monomers constituting these homopolymers. These polyester resins can be used either individually or in combination of two or more thereof.

The polyamide which can be used as a core of the thermally bonding fibers making up nonwoven fabric A includes nylon 6, nylon 66, nylon 2, nylon 3, nylon 4, nylon 7, nylon 11, nylon 12, nylon 610, and copolymers comprising any one or more of the monomers constituting these homopolymers. These polyamide resins can be used either individually or as a combination of two or more thereof.

The sheath can be made of the polymers (1) to (3) described above either individually or as a mixture of two or more thereof. Mixtures comprising at least one of these polymers and at least one of polypropylene, polyethylene, and α-olefin polymers are also useful.

The copolymer mainly comprising propylene (1) includes an ethylene-propylene copolymer, an ethylene-butene-1-propylene terpolymer, and the like, each having a propylene content of 80 to 98% by weight and an ethylene content of 2 to 20% by weight. These propylene copolymers can be used either individually or in a combination of two or more thereof.

The copolymer mainly comprising ethylene (2) includes an ethylene-vinyl acetate copolymer, an ethylene-ethyl acrylate copolymer, and an ethylene-methyl acrylate copolymer, with an ethylene-ethyl acrylate copolymer having an ethylene content of 70 to 95% by weight and an ethyl acrylate content of 5 to 30% by weight being preferred. These ethylene copolymers can be used either individually or as a combination of two or more thereof.

The low-density polyethylene (3) includes high pressure processed low-density polyethylene, a linear low-density polyethylene that is an ethylene-α-olefin copolymer, and low-density polyethylene or an ethylene-α-olefin copolymer that are produced by use of a single site catalyst. An ethylene homopolymer and an ethylene-α-olefin copolymer which are produced by use of a single site catalyst and have a density of 0.85 to 0.94 g/cm³, particularly 0.86 to 0.88 g/cm³, are preferred. They can be used either individually or as a combination of two or more thereof.

The core-sheath type thermally bonding conjugate fibers making nonwoven fabric A preferably have a core to sheath volume ratio of 1:0.25 to 4, still preferably 1:0.5 to 1.5, and a fineness of 0.5 to 25 dtex, particularly 2 to 15 dtex.

Next, nonwoven fabric B will be described. The polyester which can be used as a core of the core-sheath type thermally bonding conjugate fibers making up nonwoven fabric B includes polyethylene terephthalate, polybutylene terephthalate, polyethylene naphthalate, polyhexamethylene terephthalate, polytetramethylene terephthalate, poly-1,4- dimethylcyclohexane terephthalate, polypivalolactone t, and copolyesters comprising any one or more of the monomers constituting these homopolymers. These polyester resins can be used either individually or in combination of two or more thereof.

The polyamide which can be used as a core of the thermally bonding fibers making nonwoven fabric B includes nylon 6, nylon 66, nylon 2, nylon 3, nylon 4, nylon 7, nylon 11, nylon 12, nylon 610, and copolymers comprising any one or more of the monomers constituting these homopolymers. These polyamide resins can be used either individually or as a combination of two or more thereof.

The high-density polyethylene which can be used as a sheath preferably has a melt flow rate of 20 g/10 min or more, particularly 25 to 50 g/10 min, and a density of 0.92 to 0.97 g/cm$^3$.

The core-sheath type thermally bonding conjugate fibers making nonwoven fabric B preferably have an average fineness of 6.6 to 25 dtex, particularly 8 to 15 dtex.

Nonwoven fabrics A and B are each thermally bonded nonwoven fabric in which the individual core-sheath type thermally bonding conjugate fibers are heat-bonded at their intersections. More specifically, the sheaths of the conjugate fibers are heat-fused to each other at the intersections.

The sheet for absorbent articles according to the present invention can be used as a member of an absorbent layer of an absorbent article, for example.

Having the above-described constitution, the sheet of the present invention, when used in an absorbent article, is capable of effectively preventing the absorbent article from being distorted or twisted in the planar direction as worn thereby securing a good fit to a wearer's body and leakproofness.

Where used in an absorbent layer of an absorbent article, the sheet may be disposed with either of its MD (the direction of fiber orientation) or CD being in the longitudinal direction of the absorbent layer. With productivity taken into consideration, it is preferred for the sheet to be disposed with its MD in the longitudinal direction of the absorbent layer (absorbent member).

A preferred process for producing the sheet for absorbent articles according to the present invention will be described with reference to the sheet comprising nonwoven fabric A or B.

The sheet can be produced by a process including a step of heat treating a fiber web and a step of compressing (a) the fiber web before being heat-treated or (b) a thermally bonded nonwoven fabric obtained by heating the fiber web to reduce the thickness of the fiber web (a) or the thermally bonded nonwoven fabric (b) to 20 to 80% of the original thickness. If the degree of compression is less than 20%, no effect is produced on improvement of recovery. If it exceeds 80%, the sheet is shaped like film and, when used in an absorbent article, will give poor fit and discomfort while worn.

The step of heat treating is carried out by an air-through method which is usually practiced in the manufacture of thermally bonded nonwoven fabric.

The step of compressing (hereinafter sometimes referred to as a thickness control step) is applied to either (a) a fiber web before being heat treated or (b) a sheet obtained by thermally bonding the fiber web by, for example, an air-through method. The thickness control step is carried out by applying pressure to (a) the fiber web or (b) the thermally bonded sheet with an embossing roll and a like means usually employed for pressing nonwoven fabric with no particular restriction. The configuration of projections (bosses) on the embossing roll is not particularly limited.

Where the fiber web or the thermally bonded sheet is pressed with a flat roll in the thickness control step, the linear pressure to be given is preferably 5 to 80 cN/cm. Where an embossing roll is used for pressing, the linear pressure is preferably 100 to 500 N/cm.

It is preferred that the embossing roll be heated to a temperature Tr in a range: (T-80)° C.<Tr° C.<T° C., wherein T is the melting point of the sheath of the core-sheath type thermally bonding conjugate fibers.

The third aspect of the present invention, i.e., an absorbent article, is described below with particular reference to a panty liner.

Figure 1:
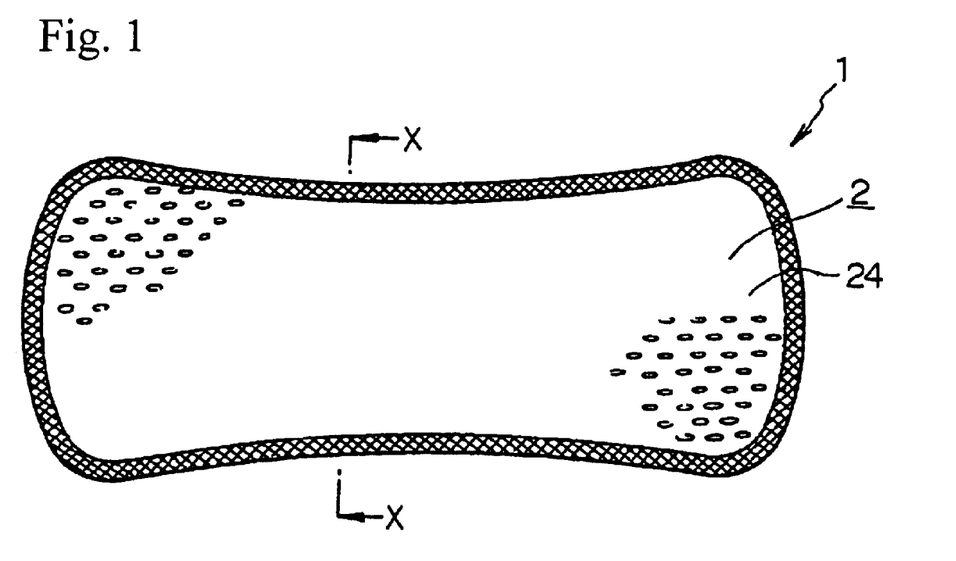
FIG. 1 is a plan view of an embodiment of the present invention.
Figure 2:
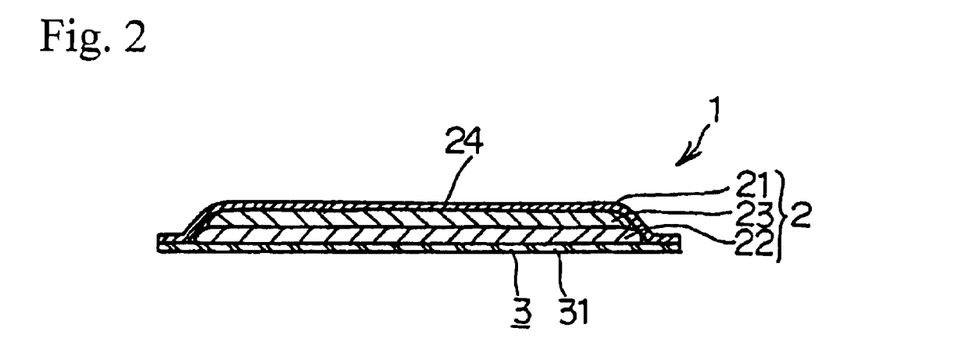
FIG. 2 is a cross section of FIG. 1 along X—X line.

The panty liner 1 shown in FIGS. 1 and 2 has a substantially rectangular shape and comprises a liquid retentive absorbent layer 2 and a liquid impermeable leakproof layer 3, wherein the absorbent layer 2 has a sheet 23 which is the above-described sheet for absorbent articles according to the present invention.

The sheet 23 is disposed under the surface layer forming the wearer's body side 24 of the panty liner 1. In detail, the absorbing layer 2 comprises a liquid permeable topsheet 21, a liquid retentive absorbent member 22, and the sheet 23 sandwiched in between the topsheet 21 and the absorbent member 22. The leakproof layer 3 comprises a moisture permeable and liquid impermeable back sheet 31. The topsheet 21 is fixed to the back sheet 31 at all the periphery thereof so that the absorbent layer 2 and the leakproof layer 3 are fixed together. While not shown, a pressure-sensitive adhesive is applied onto the back side of the leakproof layer 3 to attach the panty liner 1 to underwear on use.

The topsheet 21, the back sheet 31, and the absorbent member 22 of the panty liner 1 can be fabricated of the materials commonly employed in general sanitary napkins.

The panty liner 1 provided in this embodiment can be used as attached to underwear in the same manner as with general panty liners. While worn, the panty liner 1 having the above-described constitution is prevented from being distorted, ensuring a good fit to a wearer's body and causing no leakage.

The panty liner 1 can be produced by superposing on the back sheet 31, the absorbent member 22, the sheet 23, and the topsheet 21 in this order in the same manner as with general panty liners, and adhering the topsheet 21 and the back sheet 31 at the periphery by heat sealing, etc.

Another preferred embodiment of the absorbent article according to the present invention (fourth aspect) will be described with reference to the panty liner.

Figure 3:
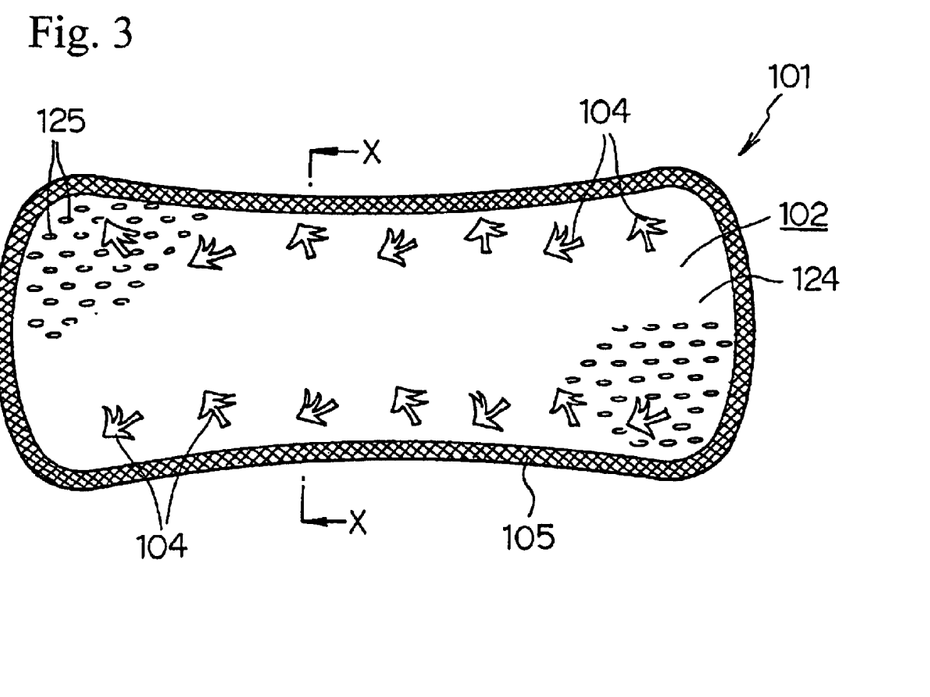
FIG. 3 is a plan view of another embodiment of the present invention.
Figure 4:
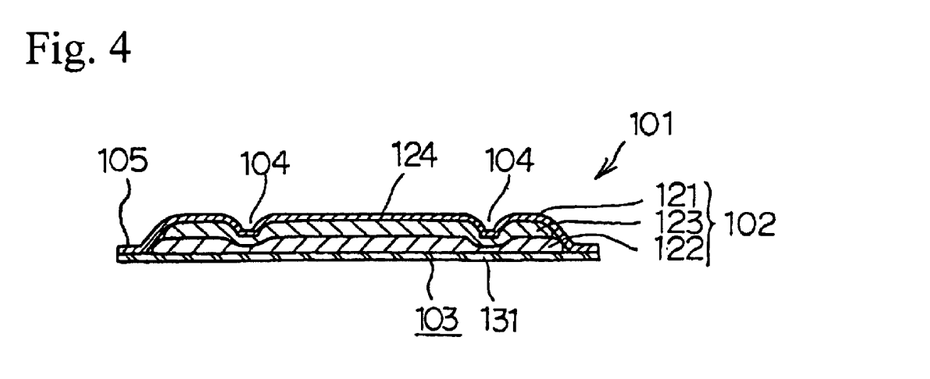
FIG. 4 is a cross section of FIG. 3 along X—X line.

As shown in FIGS. 3 and 4, the panty liner 101 is substantially rectangular and has a liquid retentive absorbent layer 102 and a liquid impermeable leakproof layer 103, wherein the absorbent layer 102 comprises an elastic layer 123 which is disposed under the surface layer forming the wearer's body side 124 of the panty liner 101.

The elastic layer 123 has an elastic recovery force of 0.7 cN or more, preferably 0.8 to 4 cN, still preferably 1 to 2 cN, and the panty liner 101 has a compressive strain of less than 5%, preferably 1 to 4%, in the width direction thereof. If the elastic recovery force of the elastic layer is less than 0.7 cN, the absorbent article has poor conformity to the contour of a wearer's body, giving poor fit. If the compressive strain of the absorbent article in the width direction exceeds 5%, it hardly restores from a distorted state, leaving untidy folds.

The elastic recovery force and the compressive strain in the width direction can be measured as follows.

Measurement of Elastic Recovery Force:

A 45 mm wide and 140 mm long strip is cut out of an elastic sheet of an absorbent article with the longitudinal direction of the strip agreeing with the longitudinal direction of the absorbent article. Because of the limited size of a sample article, the longitudinal edges of the strip may have a semicircular or trapezoidal shape. The strip is rolled with its length in the peripheral direction to make a cylinder having a lap of about 5 mm width. The lap is fastened with staples (No 10-1M, available from Max Co., Ltd.) at three positions 10 mm apart from each other, the staples being in parallel with the peripheral direction.

The cylindrical specimen (initial height: 45 mm) is set on a Tensilon compression tester (RTM-25, supplied by Toyo Baldwin) and compressed with a compression plate initially set a little higher than the specimen (at a height of about 47 mm) at a compressing speed of 50 mm/min in the axial direction of the cylinder. After compressing the specimen to a height of 30 mm (downstroke), the compressing plate was then moved upward to the initial position at the same speed to let the specimen restore the height (upstroke). The up-and-down double stroke makes one measurement. The measurement was made on at least two specimens per sample. The stress at a height of 40 mm in the upstroke is recorded, and an average of the results obtained from two or more specimens is taken as an elastic recovery force.

Measurement of Compressive Strain in Width Direction:

A 45 mm width and 140 mm long strip is cut out of an absorbent article with its longitudinal direction agreeing with the longitudinal direction of the absorbent article and made into a cylindrical specimen in the same manner as in the measurement of elastic recovery force. The specimen was given an up-and-down stroke of compression in the same manner, and the stress of the specimen vs. the position of the plate in the double stroke was recorded to make a chart. The difference between the height of the compression starting position in the downstroke (45 mm) and the height at a stress relaxation point (a position where the stress of the specimen becomes zero) in the upstroke is read from the chart. The measurement is made on at least two specimens per sample, and an average (mm) of the measured values is applied to the following equation to obtain a compressive stress in the width direction.

$$\text{Compressive stress in the width direction} = \frac{\text{average of measured values}}{45 \text{ mm}} \times 100$$

It is preferred for the panty liner 101 as an absorbent article to have an elastic recovery force of 4 cN or more, particularly 9 cN or more, especially 12 cN or more, for obtaining improved fit to a wearer's body. The elastic recovery force of an absorbent article will hereinafter be referred to as a product elastic recovery force. The product elastic recovery force is measured as follows.

Measurement of Product Elastic Recovery Force:

A specimen was prepared in the same manner as in the measurement of compressive strain in the width direction and given an up-and-down stroke of compression in the same manner to prepare a chart of the stress of the specimen vs. the position of the plate in the double stroke. The stress at a height of 40 mm in the upstroke is read. The measurement is made on at least two specimens per sample, and an average of the measured values is taken as a product elastic recovery force. In case where an absorbent article has compressed parts as in the embodiment hereinafter described, the measurements of compressive strain in the width direction (of the absorbent article) and the product elastic recovery force are made on specimens having the compressed parts, while the elastic recovery force of the elastic layer and the buckling strength (of the elastic layer) hereinafter described are measured on specimens having no such compressed parts if possible.

In the panty liner 101, the absorbent layer 102 comprises a liquid permeable topsheet 121, which forms the surface layer, a liquid retentive absorbent member 122, and the elastic layer 123 which lies between the topsheet 121 and the absorbent member 122. Interposed between the topsheet 121 and the absorbent member 122, the elastic layer 123 brings about improved touch and cushioning properties. The leakproof layer 103 comprises a liquid impermeable back sheet 131. The topsheet 121 is fixed to the back sheet 131 at all the periphery thereof so that the absorbent layer 102 and the leakproof layer 103 are fixed together. The absorbent member 122 is made slightly smaller in size than the topsheet 121 so that the topsheet 121 and the back sheet 131 may be joined directly to form peripheral portion 105 having no absorbent member 122 around the panty liner 101. While not shown, a pressure-sensitive adhesive is applied onto the back side of the leakproof layer 103 for fixing the panty liner 101 to underwear.

In order for the elastic layer 123 to have the above-specified elastic recovery force and/or for the panty liner 101 to have the above-specified compressive strain in the width direction, it is preferred that the elastic layer 123 be made of a foamed material, a dry processed pulp sheet, nonwoven fabric, etc. In particular, the nonwoven fabric for use as the elastic layer is preferably made up of one or more kinds of known resin fibers, such as polyethylene, polypropylene, polyester, nylon, and polyamide. From the aspect of production process, thermally bonded nonwoven fabric, spun-bonded nonwoven fabric, needle punched nonwoven fabric and the like can be used. Preferred is thermally bonded nonwoven fabric comprising conjugate fibers (e.g., core-sheath type conjugate fiber) having a fineness of 1 to 10 dtex, preferably 3 to 7 dtex.

It is preferred that the nonwoven fabric for use as the elastic layer 123 has increased elasticity and/or increased stiffness by any one of, preferably two or more, of the methods (i) to (iv) described below, in which "elasticity/stiffness" means elasticity and/or stiffness.

i) Elasticity/Stiffness by Fiber

Fiber of resins with high elasticity/stiffness, such as polypropylene, polyester and polyurethane, are used to obtain improved elasticity/stiffness (effect by fiber).

ii) Uniformity in Fiber Orientation

Since the elasticity/stiffness of nonwoven fabric depends on the orientation direction of constituent fibers, the elasticity/stiffness can be improved by orienting the constituent fibers in all directions at random (effect by sheet structure).

iii) Recovery of Network Structure

The network structure surrounding the bonded intersections of fibers is strengthened and/or immobilized to enhance the recover properties of the free portions between the bonded intersections, thereby improving the elasticity/stiffness (effect by sheet structure).

iv) Densifying of Sheet

The sheet is densified by using crimped fibers having a three-dimensional structure, making the fiber orientation uniform, and increasing the fiber intersections to be bonded, thereby improving elasticity/stiffness (effect by fiber).

While any one of the methods (i) to (iv) realizes the above-specified elastic recovery properties of the elastic layer, it is particularly preferred to use a combination of (i) and (iii), a combination of (i) and (iv) or a combination of (ii) and (iv), which produces both the effect by fiber and the effect by sheet structure.

It is preferred for the nonwoven fabric for use as the elastic layer 123 be hydrophilic. Hydrophilic nonwoven fabric can be obtained by a method comprising using fibers previously treated with a hydrophilic lubricant, a method comprising incorporating a hydrophilic lubricant into the fiber-forming resin (the lubricant bleeds out), a method comprising treating nonwoven fabric with a hydrophilic lubricant, or a like method. The hydrophilic nonwoven fabric preferably has a contact angle with ion-exchanged water of 70° or smaller, particularly 50° or smaller. The contact angle is measured as follows.

Measurement of Contact Angle:

Measurement is made with a contact angle meter (CA-S Micron 2, supplied by Kyowa Kaimen Kagaku K.K.) according to a fiber method (at a magnification of 300). A camera (Nicon F80) is set on the meter in the prescribed manner and focused on a sample fiber. Water is sprayed onto the fiber. Five seconds later, a photograph is taken of the fiber on an ASA 100 film. The contact angle is measured on selected five sites showing a water droplet clearly (both ends of a droplet are clear) to obtain an average.

Where nonwoven fabric having improved elasticity/stiffness by the method (ii) alone or in combination with other method is used to make the elastic layer 123, it is preferred for the nonwoven fabric to have a ratio of the buckling strength in the CD (hereinafter "CD buckling strength") to that in the MD (hereinafter "MD buckling strength") of 0.4 to 2.5, particularly 0.8 to 1.5. While the orientation state of fibers can be measured with, for example, an orientation meter, the above-described CD/MD buckling strength ratio is used in the present invention as an index of the fiber orientation direction because nonwoven fabric generally shows higher bending resistance in the orientation direction of the constituent fibers. The buckling strength is to be a quantitative value representing the bending resistance of the elastic layer. The buckling strength is measured as follows.

Measurement of Buckling Strength:

In the above-described measurement of elastic recovery force of an elastic layer, an average maximum stress reached in the downstroke is taken as a CD buckling strength. An MD buckling strength is measured in the same manner as for the CD buckling strength, except that the 45 mm wide and 140 mm long strip for making the specimen is cut out of the nonwoven fabric with its width direction being along the longitudinal direction of an absorbent article.

As shown in FIG. 4, the absorbent layer 102 has a plurality of compressed parts 104 formed on the wearer's body side 124 by compressing at least the elastic layer 123 to bring the topsheet 121, the absorbent member 122, and the elastic layer 123 into one body. The compressed parts 104 are effective to prevent the elastic layer 123 from causing reduction in liquid attracting properties. The compressed parts 104 not only bring about improved liquid attracting properties but facilitate attraction of highly viscous matter into the absorbent member.

In this embodiment, the compressed parts 104, each having a leaf pattern, are formed by pressing the panty liner 101 from its surface side 124 to press the whole thickness of the absorbent layer 102, which also produces a decorative effect.

In general, an increased density increases the liquid attracting force but, in turn, decreases liquid permeability for passing the absorbed liquid to the lower layers. Therefore, it is desirable that the topsheet 121 on at least the compressed parts 104 be perforated to exhibit excellent absorption performance. In this particular embodiment shown, the topsheet 121 is perforated to have a large number of through-holes 125 over the entire area thereof except the peripheral portion 105.

The compressed parts 104 preferably have a total area of 5 to 50% based on the entire area of the wearer's skin side 124 except the peripheral portion 105. With this lower limit, improvement on liquid attracting properties can be secured to prevent any liquid from remaining on the surface. With the above upper limit, deterioration in liquid permeability and touch (cushioning) can be minimized.

The compressed parts 104 each preferably have a base area (defined below) of 0.5 to 50 mm$^2$. With this lower limit, effective manifestation of the effect on liquid attracting properties is secured. With the above upper limit, hindrance to liquid passage can be minimized. The term "base area" as used herein denotes the area of the compressed part at the deepest, i.e., the area of the bottom of the depression.

While, in the embodiment shown in FIG. 3, the compressed parts 104 are made on both lateral side portions of the panty liner 101, they can be provided over the entire surface side, for example, in a dot pattern by embossing. To form the compressed parts 104 over the entire surface is advantageous for liquid attraction, while localizing the compressed parts on side portions as shown in FIG. 3 is advantageous for obtaining liquid attracting properties on the side portions and cushioning properties in the middle portion.

The effects as expected in the present invention are particularly pronounced in absorbent articles having a thickness of 4 mm or smaller, particularly 3 mm or smaller, especially 2 mm or smaller. Conventional absorbent articles with a thickness of 4 mm or less are very likely to be distorted or twisted while worn. In the present invention, the above-described construction effectively prevents such distortion from happening even if the thickness is so reduced. Further, such a thin absorbent article has improved fit, giving comfort to a wearer.

The topsheet 121, the back sheet 131, and the absorbent member 122 of the panty liner 101 can be fabricated of the same materials as commonly employed in general sanitary napkins.

The panty liner 101 provided in the above-described embodiment can be used as attached to underwear in the same manner as with general panty liners. While worn, the panty liner 101 having the above-described structure is prevented from being distorted by the action of the elastic layer, ensuring good fit to a wearer's body and causing no leak during use.

The panty liner 101 can be produced by, for example, superposing the topsheet 121 on the elastic layer 123, partially hot-pressing the laminate from the topsheet 121 side to form compressed parts 104 of prescribed shape in a prescribed pattern, superposing on the back sheet 131 the absorbent member 122 and the hot-pressed laminate, and adhering the topsheet 121 and the back sheet 131 at the periphery by, for example, heat sealing.

While the present invention has been described with particular embodiments of the first to fourth aspects, these embodiments should not be deemed as limiting the invention, and various changes and modifications can be made therein. For example, the present invention is applicable to sanitary napkins, disposable diapers, and adult incontinence pads as well as panty liners. The position of the sheet 23 or the elastic layer 123 in the absorbent layer 2 or 102, respectively, is not particularly limited, provided that it should not form the surface side 24 or 124 which is to be brought into contact with a wearer's skin. That is, the sheet 23 or the elastic layer 123 can be the undermost layer in the absorbing layer 2 or 102. Further, a laminate of the absorbent member 22 or 122 and the sheet 23 (which may be backed with another sheeting) or the elastic layer 123 is bent along the longitudinal direction to make an inverted "V" shape when seen from the edge side, and the periphery of the inverted V-shaped laminate is joined with a flat back sheet 31 or 131 to produce a sanitary napkin whose cross section has an inverted "V" shape. The particulars of the above-described embodiments are interchangeable among themselves.

The present invention will now be illustrated in greater detail by way of Examples, but it should be understood that the present invention is not construed as being limited thereto.

Examples of 1st to Third Aspect:

EXAMPLES 1 TO 4 AND COMPARATIVE EXAMPLE 1

A fiber web having the fiber composition shown in Table 1 below was thermally fused by an air-through method at the heating temperature shown in Table 1 to prepare nonwoven fabric.

Abbreviations used in Table 1 have the following meanings.

PET: polyethylene terephthalate

E-P: ethylene-propylene copolymer having a propylene content of 95.5 wt % and an ethylene content of 4.5 wt %

EEA: ethylene-ethyl acrylate copolymer having an ethylene content of 80 wt % and an ethyl acrylate content of 20 wt %

PP: polypropylene

VLDPE: mixture of an ethylene-α-olefin copolymer obtained by using a single site catalyst and polyethylene PE20: polyethylene having an MFR of 20 g/10 min.

PE12: polyethylene having an MFR of 12 g/10 min.

TABLE 1

|  | Example | | | | | Comparative |
| --- | --- | --- | --- | --- | --- | --- |
|  | 1 | 2 | 3 | 4 | 5 | Example 1 |
| Constituent Fiber (core-sheath type thermally bonding conjugate fiber): | | | | | | |
| Resin | PET/E-P | PET/EEA | PP/VLDPE | PET/PE20 | PET/E-P | PET/PE12 |
| Resin Ratio (vol %) | 40/60 | 50/50 | 50/50 | 40/60 | 40/60 | 40/60 |
| MFR | — | — | — | 20 | — | 12 |
| Fineness (dtex) | 4.4 | 5.5 | 5.5 | 11 | 4.4 | 3.3 |
| Crimp | machine | machine | machine | machine | machine | machine |
| Nonwoven Fabric: | | | | | | |
| Heating Temp. (° C.) | 148 | 148 | 137 | 137 | 148 | 137 |
| Basis Weight (g/m$^2$) | 40 | 40 | 40 | 40 | 40 | 40 |
| Thickness (mm) | 0.83 | 0.75 | 0.53 | 0.62 | 0.35 | 0.53 |
| Recovery Force (cN) | 2.5 | 2.0 | 2.0 | 1.5 | 4.0 | 0.5 |
| Compressive Strength (cN) | 18.6 | 20.6 | 20.6 | 20.7 | 35.5 | 31.1 |

An absorbent article shown in FIG. 1 was prepared by using the resulting nonwoven fabric as a sheet 23 and tested organoleptically. As a result, the absorbent articles of Examples 1 to 4 did not undergo distortion nor twist while worn, retaining good fit or comfort and excellent leakproofness. To the contrary, the product of Comparative Example 1 was distorted while being worn, giving discomfort to a wearer.

EXAMPLE 5

A fiber web having the fiber composition shown in Table 1 was thermally fused by an air-through method at the heating temperature shown in Table 1. The resulting sheet was 50% compressed with a flat roll under a linear pressure of 40 g/cm to prepare nonwoven fabric as a sheet for absorbent articles.

An absorbent article shown in FIG. 1 was prepared by using the resulting sheet and tested organoleptically. As a result, the absorbent article did not undergo distortion nor twist while worn, retaining good fit or comfort and excellent leakproofness.

Examples and Comparative Examples of the 4th Aspect:

EXAMPLES 6 TO 11 AND COMPARATIVE EXAMPLES 2 TO 4

The members described below and shown in Table 2 below were superposed in the top-to-bottom order of a topsheet, an elastic layer, and an absorbent member (Examples 6 to 11 and Comparative Examples 2 and 4) or a topsheet and an absorbent member (Comparative Example 3). A breathable and leakproof sheet (KTF-37, available from Mitsubishi Chemical Corp.) was disposed under the absorbent member. Every adjacent members were adhered by applying 5 g/m$^2$ of a hot-melt adhesive in a spiral pattern (a hot-melt adhesive applied to a strippable substrate in a spiral pattern could be transferred) to make a 57 mm wide and 140 mm long absorbent article having the shape shown in FIG. 3. The absorbent articles of Examples 8 to 11 had compressed parts 104 as shown in FIG. 3, except that the individual compressed parts of Examples 8, 9 and 11 had a circular shape (the individual compressed parts of Example 10 had a leaf shape). The ratio of the total area of the compressed parts to the entire area of the wearer's skin side was obtained. The results are shown in Table 2.

Members Used in the Absorbent Articles:

Topsheet 1: Nonwoven fabric comprising PET/PE fibers having a basis weight of 25 g/m², the same member as used as a topsheet of a commercially available panty liner (Lorie Panty Liner (non-fragrant type), available from Kao Corp.)

Topsheet 2: Commercially available nonwoven fabric (CotAce C03OS/A25, available from Unitika, Ltd.)

Elastic Layer 1: Nonwoven fabric prepared by thermally fusing a web of fibers NBF(SH), available from Daiwabo Co., Ltd (fineness: 4.4 dtex; average length: 51 mm), having a basis weight of 40 g/m² by an air-through method at a temperature of 148° C. and treating the nonwoven fabric with a hydrophilic lubricant according to Japanese Patent Laid-Open No. 309111/93. The resulting nonwoven fabric (elastic layer 1) had a thickness of 0.57 mm, an elastic recovery force of 0.78 cN, and a CD/MD buckling strength ratio of 0.29. The nonwoven fabric had improved elasticity/stiffness according to the above-described method (i).

Elastic Layer 2: Nonwoven fabric prepared in the same manner as for elastic layer 1, except for using a web of fibers NBF(SP) (available from Daiwabo Co., Ltd.; fineness: 4.4 dtex; average length: 51 mm) having a basis weight of 40 g/m². The nonwoven fabric (elastic layer 2) had a thickness of 0.55 mm, an elastic recovery force of 1.18 cN, and a CD/MD buckling strength ratio of 0.30. Elastic layer 2 had improved elasticity/stiffness according to the above-described methods (i) and (iii).

Elastic Layer 3: Nonwoven fabric prepared as follows. A web of fibers NBF(SH) (available from Daiwabo Co., Ltd.; fineness: 2.2 dtex; average length: 51 mm) having a basis weight of 10 g/m² and a web of fibers NBF(SP) (available from Daiwabo Co., Ltd.; fineness: 4.4 dtex; average length: 51 mm) having a basis weight of 20 g/m² were superposed on each other to prepare a laminate web having a total basis weight of 30 g/m². The laminate web was thermally fused by an air-through method at a heating temperature of 148° C. to prepare nonwoven fabric, which was then treated with a hydrophilic lubricant in the same manner as for elastic layer 1. Elastic layer 3 had a thickness of 0.48 mm, an elastic recovery force of 0.88 cN, and a CD/MD buckling strength ratio of 0.34. Elastic layer 3 had improved elasticity/stiffness by the above-described methods (i) and (iii).

Elastic Layer 4: Nonwoven fabric prepared as follows. A web of fibers NBF(SH) (available from Daiwabo Co., Ltd.; fineness: 2.2 dtex; average length: 51 mm) having a basis weight of 10 g/m² and a web of 1:1 mixed fibers of NBF(SH) (available from Daiwabo Co., Ltd.; fineness: 2.2 dtex; average length: 51 mm; three-dimensional crimped fibers) and PET fibers Tetoron (available from Teijin Ltd.; fineness: 8.8 dtex; average length: 51 mm) and having a basis weight of 30 g/m² were superposed on each other to prepare a laminate web having a total basis weight of 40 g/m². The laminate web was thermally fused by an air-through method at a heating temperature of 148° C. to prepare nonwoven fabric, which was then treated with a hydrophilic lubricant in the same manner as for elastic layer 1. Elastic layer 4 thus prepared had a thickness of 0.65 mm, an elastic recovery force of 1.76 cN, and a CD/MD buckling strength ratio of 1.06. Elastic layer 4 had improved elasticity/stiffness by the above-described methods (i) to (iv).

Elastic Layer 5: Nonwoven fabric prepared by thermally fusing a web of fibers NBF(SH) (available from Daiwabo Co., Ltd.; fineness: 2.2 dtex; average length: 51 mm) having a basis weight of 25 g/m² by an air-through method at a temperature of 148° C. to prepare nonwoven fabric and treating the resulting nonwoven fabric with a hydrophilic lubricant in the same manner as for elastic layer 1. Elastic layer 5 thus prepared had a thickness of 0.26 mm, an elastic recovery force of 0.2 cN, and a CD/MD buckling strength ratio of 0.29.

Absorbent Member 1: Paper having a basis weight of 16 g/m² and a craping ratio of 10%.

Absorbent Member 2: Dry-processed pulp sheet having a basis weight of 45 g/m² (JS45HD-W, available from J Soft K.K.)

Absorbent Member 3: Two-ply paper (30 mm×120 mm) having a basis weight of 35 g/m², each ply having a craping ratio of 20%.

Absorbent Member 4: A laminate sheet having a basis weight of 50 g/m², made of a pair of pulp webs (30 mm×60 mm) having 10 g/m² of superabsorbent polymer particles (Aquaric CAW-4, available from Nippon Shokubai Co., Ltd.) scattered therebetween.

Each of elastic layers 1 to 4 had a contact angle between 50° and 60°. The thickness of elastic layers 1 to 5 and the final products (absorbent articles) was measured with a thickness gauge ID-C112CB (supplied by Mitsutoyo K.K.) to which a measuring part of 30 mm in diameter was attached to give a load of about 10 cN.

The compressive strain in the width direction and the product elastic recovery force of the absorbent articles obtained in Examples 6 to 11 and Comparative Examples 2 to 4 were measured according to the methods previously described. Further, the absorbent articles were evaluated for non-liability to distortion and absorption performance in accordance with the following test methods. The results of the measurement and evaluation are shown in Table 2.

Evaluation of Non-Liability to Distortion:

A ten member panel were asked to use the absorbent articles of Examples 6 to 11 and Comparative Examples 2 to 4 (test sample) and, for reference, Lorie Panty Liner (non-fragrant type, "non-distortion stitches", available from Kao Corp. July, 1999), to make a judgement which of the test sample and the reference sample is less liable to distortion and to grade on the following A-to-E scale. Two articles per sample were used by each panel member.

A: The test sample is less liable to distortion.

B: The test sample is somewhat less liable to distortion.

C: The test sample and the reference sample are equal in liability to distortion.

D: The reference sample is somewhat less liable to distortion.

E: The reference sample is less liable to distortion.

The difference between the number of panel members who graded A or B (the number of panel members who approved of the test sample) and the number of panel members who graded D or E (the number of panel members who approved of the reference sample) (the former—the latter) was taken as an index for judging non-liability to distortion. The index of 5 or greater was rated "excellent", 3 to 4 "good", 1 to 2 "medium", and 0 or smaller "bad".

Evaluation of Absorption Performance:

The absorbent articles prepared in Examples 6 to 11 and Comparative Examples 2 to 4, which had the laminate structure of topsheet/(elastic layer)/absorbent member/back sheet (hereinafter referred to type A), and those having the same structure as type A but the absorbent member removed therefrom (hereinafter referred to type B) were tested as follows.

Five drops of a 65 wt % glycerol solution to which 0.5 wt % of food colorant Blue 1 (available from Aizen K.K.) had been added were dropped on the same point of the topsheet of the test sample from a height of 10 mm. After 5 minutes from the completion of dropping, the contour of the spread blue solution was marked and scanned with a scanning system comprising a light source (Sunlight SL-230K2, available from LPL), a stand (Copy Stand CS-5, available from LPL), a lens (24 mm/F2.8 Nikkor Lens), a CCD camera (HV-D37, available from Hitachi Electronics, Ltd.; the lens connected with an F-mount connector), and a video board (Spectra 3200, available from Canopus Co., Ltd.). The digital image information obtained were processed on image analyzing software supplied by NEXUS (ver. 3.08) to obtain the area of the spread.

The ratio of the spread area on an A type sample to that on a corresponding B type sample was obtained. The ratio of 0.8 or less was graded "good", more than 0.8 and less than 0.9 "medium", and 0.91 or more "bad".

TABLE 2

| | | Structure | | | | | Results of Product Evaluation | | | | |
|---|---|---|---|---|---|---|---|---|---|---|---|
| | | Elastic Layer | | | | | | | | | |
| | | | Elastic | | Compressed Parts | | Compressive | Elastic | | | Liquid |
| | Topsheet | Kind | Recovery Force (cN) | Absorbent Member | Total Area Ratio (%) | Area per Part (mm²) | Strain in CD (%) | Recovery Force (cN) | Thickness (mm) | Non-liability Distortion | Spread on Surface |
| Ex. 6 | 1 | 1 | 0.78 | 1 | 0 | 0 | 3.5 | 11.8 | 1.7 | good | medium |
| Ex. 7 | 2 | 4 | 1.76 | 1 | 0 | 0 | 3.6 | 9.8 | 1.6 | good | medium |
| Ex. 8 | 1 | 2 | 1.18 | 1 | 12* | 0.79 | 2.5 | 17.6 | 2 | excellent | good |
| Ex. 9 | 1 | 3 | 0.88 | 3 | 27* | 1.8 | 2.9 | 15.5 | 1.9 | excellent | good |
| Ex. 10 | 1 | 4 | 1.76 | 4 | 7** | 36 | 3 | 18.9 | 2.5 | excellent | good |
| Ex. 11 | 2 | 2 | 1.18 | 2 | 36* | 0.79 | 3.6 | 7.9 | 1.6 | medium | good |
| Comp. Ex. 2 | 1 | 5 | 0.2 | 1 | 0 | 0 | 6.5 | 3.9 | 1.5 | bad | medium |
| Comp. Ex. 3 | 1 | — | — | 2 | 0 | 0 | 6.7 | 2.9 | 1.3 | bad | good |
| Comp. Ex. 4 | 2 | 1 | 0.78 | 5 | 0 | 0 | 12 | 1.5 | 4.3 | bad | bad |

Note:
*Formed over the entire surface
**Formed on both lateral sides

In Examples 6 to 11, the elastic recovery force of the elastic layer and the width direction compressive strain of the panty liner are within the respective ranges specified in the present invention so that the absorbent articles exhibit satisfactory resistance against distortion while worn. In particular, the absorbent articles of Examples 8 to 10 have a width direction compressive strain of 3% or less by virtue of the effects of the compressed parts and the topsheet and were highly approved of by the panel members. Further, the absorbent articles of Examples 8 to 11 which have compressed parts exhibited satisfactory absorption performance.

On the other hand, Comparative Example 2 in which the elastic layer has a low elastic recovery force and Comparative Example 3 having no elastic layer were not exactly approved of by users with regard to liability to distortion. The absorbent article of Comparative Example 4 which has a large compressive strain in the width direction did not find much approval, either.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A sheet which gives an absorbent article improved recovery from distortion, comprising:
    thermally bonded nonwoven fabric containing 70% by weight or more of core-sheath type thermally bonding conjugate fibers which are thermally fused together at their intersections, wherein the core comprises a polyester, and the sheath comprises a copolymer mainly comprising propylene or a copolymer mainly comprising ethylene,
    wherein said sheet has a recovery force of 0.7 cN or more in the cross direction, a compressive strength of 100 cN or less, and a basis weight of 20 g/m² or more.

2. An absorbent article comprising a liquid retentive absorbent layer and a liquid impermeable leakproof layer, wherein said absorbent layer has the sheet for an absorbent article described in claim 1.

3. A sheet which gives an absorbent article improved recovery from distortion, comprising:
    thermally bonded nonwoven fabric, an entire thickness of the thermally bonded nonwoven fabric containing 70% by weight or more of core-sheath type thermally bonding conjugate fibers which are thermally fused together at their intersections, wherein the core comprises polyester or polyamide, the sheath consists of high-density polyethylene, and the conjugate fibers have an average fineness of 8 dtex to 22 dtex,
    wherein said sheet has a recovery force of 0.7 cN or more in the cross direction, a compressive strength of 100 cN or less, and a basis weight of 20 g/m² or more.

4. The sheet according to claim 3, wherein said high-density polyethylene has a melt flow rate of 20 g/10 mm or more and a density of 0.92 to 0.97 g/cm³.

5. An absorbent article comprising a liquid retentive absorbent layer and a liquid impermeable leakproof layer, wherein said absorbent layer has the sheet for an absorbent article described in claim 3.

6. An absorbent article comprising liquid retentive absorbent layer and a liquid impermeable leakproof layer, wherein said absorbent layer is provided with the sheet according to claim 3.

7. An absorbent article which has a substantially longitudinal shape and comprises a liquid retentive absorbent layer and a liquid impermeable leakproof layer, wherein said absorbent layer has a surface layer that is to be brought into contact with a wearer's skin and an elastic layer disposed under said surface layer, said elastic layer being a thermally bonded nonwoven fabric containing 70% by weight or more of core-sheath type thermally bonding conjugate fibers which are thermally fused together at their intersections, the core comprises a polyester, and the sheath comprises a copolymer mainly comprising propylene or a copolymer mainly comprising ethylene, said elastic layer having an elastic recovery force of 0.7 cN or more, and said absorbent article has a compressive strain of less than 5% in the width direction.

8. The absorbent article according to claim 7, wherein said absorbent layer comprises a liquid permeable topsheet which forms said surface layer, a liquid retentive absorbent member, and said elastic layer lying between said topsheet and said absorbent member.

9. The absorbent article according to claim 8, wherein said absorbent layer has a plurality of compressed parts on the side of said surface layer, said compressed parts being formed by compressing at least said elastic layer to unite said topsheet, said absorbent member and said elastic layer into one body in said parts.

10. The absorbent article according to claim 7, which has a thickness of 4 mm or smaller.

11. The absorbent article according to claim 7, wherein the sheath consists of said low-density polyethylene having a density of 0.85 to 0.94 g/cm$^3$.

12. A sheet which gives an absorbent article improved recovery from distortion, comprising:

thermally bonded nonwoven fabric containing 70% by weight or more of core-sheath type thermally bonding conjugate fibers which are thermally fused together at their intersections, wherein the core comprises a polyolefin, polyester or polyamide, and the sheath comprises low-density polyethylene, said low-density polyethylene having a density of 0.86 to 0.88 g/cm$^3$, wherein said sheet has a recovery force of 0.7 cN or more in the cross direction, a compressive strength of 100 cN or less, and a basis weight of 20 g/m$^2$ or more.

13. An absorbent article which has a substantially longitudinal shape and comprises a liquid retentive absorbent layer and a liquid impermeable leakproof layer, wherein said absorbent layer has a surface layer that is to be brought into contact with a wearer's skin and an elastic layer disposed under said surface layer, said elastic layer being a thermally bonded nonwoven fabric containing 70% by weight or more of core-sheath type thermally bonding conjugate fibers which are thermally fused together at their intersections, the core comprises a polyolefin, polyester or polyamide, and the sheath comprises low-density polyethylene, said low-density polyethylene having a density of 0.86 to 0.88 g/cm$^3$, said elastic layer having an elastic recovery force of 0.7 cN or more, and said absorbent article has a compressive strain of less than 5% in the width direction.

14. A sheet which gives an absorbent article improved recovery from distortion, comprising:

thermally bonded nonwoven fabric, an entire thickness of the thermally bonded nonwoven fabric consisting of core-sheath type thermally bonding conjugate fibers, which are thermally fused together at their intersections, wherein the core comprises polyester or polyamide, the sheath consists of high-density polyethylene, and the conjugate fibers have an average fineness of 8 dtex to 22 dtex, wherein said sheet has a recovery force of 0.7 cN or more in the cross direction, a compressive strength of 100 cN or less, and a basis weight of 20 g/m$^2$ or more.

15. An absorbent article comprising liquid retentive absorbent layer and a liquid impermeable leakproof layer, wherein said absorbent layer is provided with the sheet according to claim 14.

* * * * *